United States Patent [19]

Kiamil

[11] Patent Number: 5,316,762
[45] Date of Patent: May 31, 1994

[54] EMULSION POLYMERIZED POLYMER

[75] Inventor: Sinan Kiamil, Basingstoke, United Kingdom

[73] Assignee: Scholl plc, Windsor, United Kingdom

[21] Appl. No.: 796,538

[22] Filed: Nov. 21, 1991

[51] Int. Cl.$^5$ ............................................. A61K 47/32
[52] U.S. Cl. .................. 424/78.35; 424/78.37; 424/445; 526/213; 526/304
[58] Field of Search .................. 424/445, 78.35, 78.37; 526/213, 304

[56] References Cited

U.S. PATENT DOCUMENTS

| | | | |
|---|---|---|---|
| 3,480,578 | 11/1969 | Witt | 424/78.35 |
| 4,286,081 | 8/1981 | Mikofalvy et al. | 526/213 |
| 4,692,366 | 9/1987 | Mudge | 526/304 |
| 4,696,951 | 9/1987 | Junsford et al. | 526/304 |
| 4,810,751 | 3/1989 | Jellinek et al. | 526/273 |
| 4,960,777 | 2/1990 | Ball et al. | 526/213 |
| 4,963,422 | 10/1990 | Katz et al. | 526/304 |

FOREIGN PATENT DOCUMENTS 1257940 12/1971 United Kingdom .

*Primary Examiner*—Thurman K. Page
*Assistant Examiner*—Peter F. Kulkosky
*Attorney, Agent, or Firm*—Sheridan Ross & McIntosh

[57] ABSTRACT

An emulsion polymerized polymer, a process for its preparation and its use in the form of an adhesive particularly in surgical or medical dressings or plasters wherein the polymer is derived by polymerizing in an aqueous emulsion a composition comprising:

(A) a substantially water-insoluble monomer; with (B) (1) a substantially water-insoluble polar monomer; and/or (B) (2) a substantially water-insoluble polyfunctional monomer; in the presence of a substantially water-soluble surfactant which has been converted to a substantially water-insoluble form after polymerization of monomers (A) and (B).

7 Claims, No Drawings

EMULSION POLYMERIZED POLYMER

The present invention relates to an emulsion polymerised polymer, a process for its preparation and, particularly, but not exclusively, to a water-resistant adhesive containing the polymer, and to its preparation.

It is known to produce water-resistant adhesives using solution polymerisation in a non-aqueous solvent. However, in order to avoid the use of a solvent, which can be very expensive and which is capable of causing damage to the environment, it has been proposed to produce adhesives using aqueous emulsion polymerisation techniques. The disadvantage with hitherto proposed techniques is that any advantage afforded by the use of emulsion polymerisation over solution polymerisation is offset by a reduction in the water-resistance of the product of emulsion polymerisation compared with that achieved using solution polymerisation.

Emulsion polymerisation requires the use of a surfactant to form a stable emulsion of monomers -and to prevent coagulation of the product polymer. Surfactants are generally categorised into two types: either non-polymerisable, or polymerisable, that is co-polymerisable with the monomers for polymer formation. A problem which has arisen with the use of non-polymerisable surfactants is that they remain as a residue in the product polymer and, as they can be extracted by water, they make the product sensitive to water.

The use of polymerisable surfactants in salt form is described, for example, in British Patent No. 1430136. However, the use of non-polymerisable surfactants in the process described in this patent is not entirely avoided and these additional non-polyi-nerisable surfactants again have the effect of rendering the product polymer water sensitive. European Patent No. 0 099 675 also discloses the use of polymerisable surfactants. However, the use of water soluble monomers and a surfactant in the form of a salt renders the final polymer hydrophilic so that water can migrate into the polymer and again affect adhesive properties by reducing resistance to water.

We have now found it possible to avoid the above-mentioned problems and to provide a process which employs an emulsion polymerisation technique to give an adhesive product which has comparable water-resistance properties to those of solvent-based adhesives.

We have also found it possible to provide an adhesive which has good tack, cohesive and adhesive properties.

We have also found it possible to provide an adhesive which is hypoallergenic.

The above-mentioned properties make the adhesive of the present invention especially suitable for skin care applications in, for example, surgical or medical dressings and plasters where it is essential that the adhesive is water-resistant in order to maintain adhesion of the dressing or plaster to the skin. The adhesive is particularly useful in footcare applications, where there is often a high moisture environment.

According to one aspect of the present invention there is provided a process for the preparation of a polymer comprising polymerising in an aqueous emulsion (A) one or more water-insoluble monomers; with (B)(1) a polar water-insoluble monomer, and/or (B) (2) a water-insoluble polyfunctional monomer; in the presence of a water-soluble surfactant which may be converted to a water-insoluble form after polymerisation of monomers (A) and (B).

According to another aspect of the present invention there is provided a polymer derived from polymerising (A) one or more water-insoluble monomers; with (B)(1) a polar water-insoluble monomer, and/or (B) (2) a water-insoluble polyfunctional monomer; in the presence of a water-soluble surfactant which has been converted to a water-insoluble form after polymerisation of monomers (A) and (B).

In a further aspect of the invention the polymer according to the present invention is used as a water-resistant adhesive. In yet another aspect of the present invention the product of the present invention is used as a water-resistant adhesive in skin-care applications.

Various preferred features and embodiments of the invention will now be described by way of non-limiting example.

The present invention employs non-polymerisable surfactants which following an emulsion polyi-nerisation process step may be converted into an insoluble form. Thus the polymers according to this invention are not sensitive to water in that water does not effect their polymeric properties.

We have now also found that a specific combination of water-insoluble monomers used with certain non-polyi-nerisable surfactants can be used to form stable emulsions in emulsion polymerisation. By using the specific combination of monomers according to the present invention, the adhesive product polymer will possess good tack, adhesion and cohesion without having to subject the polymer to a further processing step such as compounding with tackifyers and/or plasticizers.

Surfactant

The surfactant used in the present invention is non-polymerisable. The surfactant is capable of forming a stable emulsion during the emulsion polymerisation process step, but is fugitive in the sense that subsequent to polyi-nerisation, e.g. in an extraction process to obtain a dry product polymer, the surfactant changes from a water-soluble/miscible compound to a water-insoluble/immiscible compound. The fugitive nature of the surfactant means that it avoids the probletns of conventional non-polymerisable surfactants by not rendering the polyi-nerised product sensitive to water, while still being able to form a good emulsion in the polyi-nerisation process. In addition the surfactants of the present invention may be used without the addition of additional external surfactants.

Preferably the surfactant in its water-insoluble form is a compound of formula (1) or (11):

R—COOH (I)

R—OOC—A—COOH (II)

Preferably wherein R is a linear or branched $C_{6-30}$ hydrocarbon group. Preferably R is derived from a linear or branched chain alkane, alkene or diene group with a minimum of 6 carbon atoms. Preferably the compound of formula (I) is a fatty acid, e.g. lauric acid, i.e. R is $C_{11}$, or even more preferably stearic acid, i.e. R is $C_{17}$.

A is preferably a saturated or unsaturated, linear or branched chain aliphatic or aromatic $C_{2-6}$ hydrocarbon group such that A $(COOH)_2$ is a dibasic acid capable of forming the anhydride, $A(CO)_2O$. Preferably A is an alkylene or alkenylene or phenylene group. Preferably, A is CH=CH or $C_6H_4$ or, especially, $CH_2CH_2$.

In order to act as a surfactant, preferably a salt of the compound (I) or (II) is employed, which is water-soluble/miscible. Preferred salts are ammonium or alkyl substituted ammonium salts such as trimethylammonium and triethylammonium. A particularly preferred salt is the ammonium salt.

A particularly preferred surfactant of the present invention is the ammonium salt of stearic acid. Ammonium stearate is a fugitive surfactant in that the salt will form a stable emulsion during polymerisation with the monomers of the present invention, while on heating the resulting polymer to a dry form, ammonia is liberated leaving stearic acid residues. Stearic acid is substantially water-insoluble and hence does not render the polymer water sensitive.

Thus, for example, an anionic salt of a compound of formula (I) or (II) will function as a water-soluble surfactant during the polymerisation process of the present invention. The compound can then be converted to a water-insoluble form by decomposition of the salt, preferably this decomposition occurs during heating while drying the product polymer, although the surfactant can be converted to the insoluble form using other techniques.

The polymer products of the present invention preferably contain 0.5% to 10.0% by weight, preferably 0.6% to 6% by weight, and even more preferably 1.0% to 3.0% by weight of a compound of a formula (I) or (II) e.g. after decomposition of the salt form.

The compounds of formula (II) may conveniently be prepared by reacting a dibasic acid anhydride of formula $A(CO)_2O$ with a compound of formula (III)

R-OH  (III)

wherein R is as defined above.

A preferred compound of formula (III) is stearyl alcohol.

Preferred dibasic anhydrides include succinic anhydride, maleic anhydride and phthalic anhydride.

The compounds of formula (II) may be prepared by conventional methods.

The salts of the compounds of formula (I) or (II) may be prepared by reacting the acid compound with an appropriate base. Preferred water-soluble salt compounds for use during the emulsion polymerisation step be formed by reacting the acid compound in aqueous suspension with, e.g. ammonia or optionally alkyl substituted ammonium hydroxide. Preferably the monomer salts are prepared in situ.

The Monomers

During emulsion polymerisation, radicals are generated in the aqueous medium and these transfer to monomer droplets to initiate polymer formation therein. If water-soluble monomers were to be employed, the monomers start to polymerise in aqueous solution and polymers are produced which are mainly composed of hydrophilic water-soluble polymers which thus render the polymer water sensitive. In contrast the monomers used in the present invention are substantially water-insoluble and are not prone to polymerisation in the aqueous phase. They hence give water resistant polymer products.

The present invention employs a specific combination of water-insoluble monomers to produce an adhesive which is not only water-resistant but which also has a satisfactory balance of the properties required by an adhesive, particularly for skin application, for example, tack, cohesion and adhesion.

Monomer (A)

At least one type of water-insoluble monomer (A) is employed to provide the adhesive with tack and adhesion. Such monomers which contribute towards tack and adhesion are commonly known as low Tg (glass transition temperature) monomers. Preferred water-insoluble monomers (A) according to the present inventions are acrylic or methacrylic monomers e.g. derivatives of acrylic acid. Preferably the monomer is an alkyl ester of acrylic or methacrylic acid wherein the alkyl group contains from 2 to 12 carbon atoms, preferably 3 to 10 carbon atoms and even more preferably 4 to 9 carbon atoms. Preferred alkyl acrylate monomers of this type include n-butyl acrylate, 2-ethyl acrylate, 2-ethylhexyl acrylate and other octyl acrylates.

A pressure sensitive adhesive polymer of the present invention preferably comprises 90 to 99.5% by weight of such acrylate residues, preferably 94 to 99.5% and even more preferably 97 to 99% by weight. As mentioned previously a mixture of different type (A) monomers may be used.

Monomer (B)

Cohesive strength and further adhesive strength is produced in the polymers of the present invention by employing a further water-insoluble monomer type (B) which will contribute towards these properties by inter and/or intramolecular attraction or by crosslinking the polymer. Again these monomers are substantially water-insoluble to avoid the production of hydrophilic polymers.

The monomers (B) of the present invention comprise: (B)(1) a substantially water-insoluble polar monomer; or (B)(2) a substantially water-insoluble polyfunctional monomer; or mixtures thereof.

Preferred monomers of type (B)(1) are mono substituted acrylamides and methacrylamides such as N-isobutoxymethyl methacrylamide, and N-isobutoxymethyl acrylamide; and N-alkyl substituted acrylamides and methacrylamides wherein the alkyl group contains at least 3 carbon atoms. These monomers contain groups which are capable of forming inter and/or intra interactions; are substantially water-insoluble; and polymerise at a similar rate to the other monomers used in the emulsion polymerisation process. These monomers are commonly known as high Tg monomers.

The polyfunctional monomers of type (6)(2) contribute to the cohesive strength of the adhesive by forming crosslinks. Preferred monomers include polyfunctional derivatives of acrylic and methacrylic acid. Especially preferred monomers of this type include alkanediyldiesters, for example, butanediyldiacrylate and hexanediyldiacrylate.

Preferred formulations for pressure sensitive adhesive polymers according to the present invention will now be given by way of non-limiting example.

Example (i)

39 to 59% by weight of n-butylacrylate residue, 39 to 59% by weight 2-ethylhexylacrylate residue, 0.3 to 10%, preferably 0.3 to 5%, of N-isobutoxymethylacrylamide and 1 to 5% by weight of stearic acid residues.

Example (ii)

39 to 59% by weight of n-butylacrylate residue, 39 to 59% by weight 2-ethylhexylacrylate residue, 0.3 to 10%, preferably 0.3 to 2.5%, of butanediyldiacrylate and 1 to 5% by weight of stearic acid residues.

Example (iii)

47% to 49.75% by weight of n-butylacrylate residue, 47 to 49.75% by weight 2-ethylhexylacrylate residue, 0.3 to 2.0% by weight of butanediyldiacrylate or 0.3 to 4.0% N-isobutoxymethylmethacrylamide and 1.0 to 3.0% by weight of stearic acid residues.

Example (iv)

49.125% by weight of n-butylacrylate residue, 49.125% by weight 2-ethylhexylacrylate residue, 1.75% by weight of butayediyldiacrylate and 3.0 parts by weight per hundred monoi-ner of stearic acid residues.

Example (v)

49.5% by weight of n-butylacrylate residue, 49.5% by weight 2-ethylhexylacrylate residue, 1.0% by weight of N-isobutoxymethylmethacrylamide and 2.0 parts by weight per hundred monomer of stearic acid residues.

(% by weight are to a total of 100%).

As previously mentioned the polymers of the present invention are prepared using emulsion polymerisation. This polymerisation is conveniently carried out in the presence of a free radical catalyst which is generally an aqueous free radical catalyst such as ammonium persulphate or a redox catalyst.

Again as previously mentioned the emulsion may conveniently be prepared by initially forming an aqueous solution of the water-soluble form of the surfactant, preferably the salt of a compound of formula (1) or (II) is formed in situ from a compound of formula (1) or (11) and a suitable base.

The combination of monomers of the present invention may be premixed, added to the aqueous solution, and then mixed together under high shear stirring. Preferably the monomer emulsion has a solids content in the range of 15 to 60% by weight and more preferably 30 to 50%.

The resulting monomer emulsion may then be added to an aqueous solution of the free radical catalyst and polymerisation is effected by heating, typically from 80° to 950° C., under an inert atmosphere, such as nitrogeon or carbon dioxide. Advantageously, the monomer emulsion is added to the catalyst solution at intervals or continuously over a period of time throughout the polymerisation reaction.

The preferred adhesive emulsions of the present invention may contain a thickener and/or other additives conventionally used in emulsion polymers.

The resultant adhesive can be coated onto a suitable substrate, preferably by direct or transfer coating using conventional techniques. The substrate coated with the adhesive is then heated to dry the adhesive and in so doing the surfactant may be converted from a water-soluble to a water-insoluble form.

The process of the present invention will now be described further with reference to the following non-limiting examples.

Example 1: Preparation of emulsion polyacrylate adhesive

Stearic acid (2 g) was dissolved in deionised water (100 g) using concentrated aqueous ammonia solution (1 g). The pH of the solution was checked and adjusted to 10 by the addition of concentrated ammonia solution. 2-Ethylhexyl acrylate (49.5 g), n-butyl acrylate (49.5 g) and N-isobutoxymethyl methacrylamide (1 g) were added to the solution and the solution stirred with a high shear mixer to form a monomer emulsion. The monomer emulsion was added dropwise from a dropping funnel over a period of one hour to an ammonium persulphate solution (0.26 g) in 50 ml of deionised water) in a reaction flask fitted with a stirrer and a nitrogen inlet maintained at a constant temperature in the range of 80° to 90° C. by a constant temperature water bath. The polymerisation was allowed to continue for a further one and a half 1-iours to give a total reaction time of two and a half hours. The resultant polymer emulsion was cooled to 40° C., filtered and was transferred to a storage jar.

The following Table 1 lists further Examples 2–21 prepared by the method of Example 1 using different starting materials byweight in the amounts set out in the Table. In the Table the following abbreviations are used;

2-EHA: 2-ethylhexyl acrylate, n-BA: n-butyl acrylate, BDDA: butanediyldiacrylate, IBMMA: N-isobutoxymethyl methacrylamide, SA: stearic acid.

TABLE 1

| Ex No. | 2-EHA | n-BA | BDDA | IBMMA | SA |
|---|---|---|---|---|---|
| 2 | 49.25 | 49.25 | 1.5 | | 3.0 |
| 3 | 49.125 | 49.125 | 1.75 | | 3.0 |
| 4 | 49.0 | 49.0 | 2.0 | | 3.0 |
| 5 | 50.0 | 50.0 | | | 3.0 |
| 6 | 49.0 | 49.0 | 2.0 | | 1.0 |
| 7 | 49.0 | 49.0 | 2.0 | | 1.0 |
| 8 | 49.0 | 49.0 | 2.0 | | 0.5 |
| 9 | 50.0 | 50.0 | | | 1.0 |
| 10 | 49.5 | 49.5 | 1.0 | | 1.0 |
| 11 | 49.0 | 49.0 | 2.0 | | 1.0 |
| 12 | 48.5 | 48.5 | 3.0 | | 1.0 |
| 13 | 48.0 | 48.0 | 4.0 | | 1.0 |
| 14 | 49.0 | 49.0 | | 2.0 | 1.0 |
| 15 | 48.0 | 48.00 | | 4.0 | 1.0 |
| 16 | 49.0 | 49.0 | | 2.0 | 2.0 |
| 17 | 48.0 | 48.0 | | 4.0 | 2.0 |
| 18 | 49.75 | 49.75 | | 0.5 | 1.0 |
| 19 | 49.5 | 49.5 | | 1.0 | 1.0 |
| 20 | 49.25 | 49.25 | | 1.5 | 1.0 |
| 21 | 49.5 | 49.5 | | 1.0 | 2.0 |

Example 22

The polyacrylate adhesive emulsion of Example 1 was thickened by the addition of an acrylic thickener solution (Primal ASE60, 10%, available from Rohm and Haas) and was coated onto a cotton fabric by means of a blade over roll coater and dried in an air circulation oven at a temperature of 120° C. to give a dried pressure sensitive adhesive coating with an application weight per unit area of 120 gsm. The resulting medical tape adhered well to human skin under both dry and wet conditions.

The water-resistant adhesive properties of the polymers of the present invention make them especially suitable for use in surgical and medical dressings or plasters where it is important that good adhesion to the skin is maintained even when the dressing or plaster comes into contact with water. In addition, the adhesives of the present invention are found to be particularly compatible for foot care products where a high moisture environment is often encountered. Further, the adhesive is hypoallergenic, which is again important in skin care applications. In order to form surgical and medical dressings and plasters the adhesive can be coated onto the substrate material such as fabrics, needled felts, polyvinylchloride films, polyurethane films, non-woven fabrics, nets and foams, from which the dressings and plasters are formed.

It will be appreciated that the polymers of the present invention can be used in other applications in which an adhesive is required in addition to the medical and surgical field.

I claim:

1. An adhesive polymer derived from polymerizing in an aqueous emulsion a composition comprising:
   a substantially water-insoluble monomer (A) comprising $C_{2-12}$ alkyl ester of acrylic or methacrylic acid; with
   a substantially water-insoluble polar monomer (B)(1) comprising a mono substituted acrylamide or methacrylamide, or an N-alkyl substituted acrylamide or methacrylamide wherein the alkyl group contains at least 3 carbon atoms; and/or
   a substantially water-insoluble polyfunctional monomer (B)(2) comprising an alkanediyldiester, which in the presence of a substantially water-soluble surfactant consisting essentially of ammonium or alkyl substituted ammonium salt of stearic acid, is converted to a substantially water-insoluble form after polymerization of monomers (A) and (B).

2. The polymer as set forth in claim 1, wherein the adhesive polymer produced does not contain undesired water-soluble residues in the final product.

3. The polymer as set forth in claim 1, wherein the adhesive polymer adheres well to human skin under both dry and wet conditions.

4. The polymer as set forth in claim 1, wherein said polymer does not include metal salts.

5. The polymer as set forth in claim 1, wherein said polymer has good tack, cohesive, and adhesive properties.

6. The polymer as set forth in claim 1, wherein said polymer is hypoallergenic.

7. An adhesive polymer derived from polymerising in an aqueous emulsion a composition comprising:
   a substantially water-insoluble monomer (A) comprising $C_{2-12}$ alkyl ester of acrylic or methacrylic acid; with
   a substantially water-soluble polar monomer (B) (1) comprising a mono substituted acrylamide or methacrylamide, or an N-alkyl substituted acrylamide or methacrylamide wherein the alkyl group contains at least 3 carbon atoms; and/or
   a substantially water-insoluble polyfunctional monomer (B) (2) comprising an alkanedyldiester which, in the presence of a substantially water-soluble surfactant consisting essentially of an ammonium or alkyl substituted ammonium salt of stearic acid, but in the absence of metal salts, is converted to a substantially water-insoluble form after polymerisation of monomers (A) and (B), thereby producing a water-resistant, hypoalergenic, hydrophobic adhesive polymer.

* * * * *